US006916488B1

(12) United States Patent
Meier et al.

(10) Patent No.: US 6,916,488 B1
(45) Date of Patent: Jul. 12, 2005

(54) AMPHIPHILIC POLYMERIC VESICLES (75) Inventors: Wolfgang Meier, Basel (CH); Thomas Hirt, Rebstein (CH); Corinne Nardin, St. Louis (FR)

(73) Assignee: BioCure, Inc., Norcross, GA (US)

( * ) Notice: Subject to any disclaimer, the term of this patent is extended or adjusted under 35 U.S.C. 154(b) by 78 days.

(21) Appl. No.: 09/615,305

(22) Filed: Jul. 13, 2000

Related U.S. Application Data
(60) Provisional application No. 60/163,678, filed on Nov. 5, 1999.

(51) Int. Cl.⁷ .............................................. A61K 9/127
(52) U.S. Cl. ................... 424/450; 424/1.21; 424/9.321; 424/9.51; 424/489
(58) Field of Search ............... 424/450, 1.21, 424/9.321, 9.51, 417, 943; 436/829; 428/402.2; 426/489–502

(56) References Cited

U.S. PATENT DOCUMENTS

| | | | |
|---|---|---|---|
| 4,659,777 A | | 4/1987 | Riffle et al. |
| 4,661,442 A | | 4/1987 | Lukens |
| 5,080,936 A | | 1/1992 | Cerwen |
| 5,807,944 A | | 9/1998 | Hirt et al. |
| 5,874,316 A | | 2/1999 | Cornell et al. |
| 5,891,468 A | * | 4/1999 | Martin |
| 5,922,594 A | | 7/1999 | Lofas |
| 5,955,343 A | | 9/1999 | Holmes et al. |
| 6,008,184 A | * | 12/1999 | Pluyter |

FOREIGN PATENT DOCUMENTS

| | | |
|---|---|---|
| EP | 552 802 | 7/1993 |
| JP | 10 110019 | 8/1996 |

OTHER PUBLICATIONS

Benz, R. et al. *Eur. J. Biochem.* 176, 1 (1988).
Benz, R., *J. of Bacteriol.* 162(12), 722 (1985).
Discher, B. M. et al., *Science* 284, 1143 (1999).
Ding, et al., *J. Phys. Chem. B.*, 102, 6107 (1998).
Dobashi, et al., *Langmuir*, 11, 4278 (1995).
Donath, et al., *Angew. Chem. Int. Ed. Engl.*, 110(16):2324 (1998).
Donath, et al., *Nachr. Chem. Tech. Lab.* 47, 400 (1999).
Dutzler, R. et al., *Structure* 4(2), 127 (1996).
Eisenberg, B., *Acc. Chem. Res.* 31, 117 (1998).
Hajduk, D.A. et al., *J. Phys. Chem. B* 102, 4269 (1998).
Hotz, et al., *Langmuir*, 14, 1031 (1998).
Hotz, et al., *Adv. Mater.*, 10, 1387 (1998).
Huang, et al., *J. Am. Chem. Soc.*, 121, 3805 (1999).
Jenekhe, et al., *Science*, 279, 1903 (1998).
Jenekhe et al., *Science*, 283(5400) 372–5 (1999).
Kong, et al., *Polym. Adv. Technol.*, 8, 627 (1997).
Kurja, et al., *Polymer*, 34(10), 2045 (1993).
Lakey, J. H., *FEBS Letters* 278(1):31–34 (1991).
Maassen, H.–P. et al., *Makromol. Chem., Macromol. Symp.* 39, 215 (1990).
Meier, W., *Macromolecules*, 31, 2212 (1998).

(Continued)

*Primary Examiner*—Gollamudi S. Kishore
(74) *Attorney, Agent, or Firm*—Collen A. Beard

(57) ABSTRACT

Vesicles made from amphiphilic copolymers are disclosed. The amphiphilic copolymers can be ABA copolymers, where one of A and B is hydrophilic and the other is hydrophobic. AB copolymers can also be used. The copolymers may be crosslinked to form nanocapsules. Crosslinking can be accomplished using a variety of methods, including end to end polymerization of copolymers having terminal unsaturated groups. Molecules, such as membrane proteins, can be incorporated into the wall of the vesicles or nanocapsules.

20 Claims, 2 Drawing Sheets

OTHER PUBLICATIONS

Meier, W., *Langmuir*, 12, 6341 (1996).
Mueller, P, et al., *J. Phys. Chem.* 67, 534 (1963).
Müller, D. J. et al., *J. Mol. Biol.* 285, 1347 (1999).
Murtagh, et al., *Faraday Discuss. Chem. Soc.*, 81, 127 (1986).
Nikaido, H., *Molecular Microbiology* 6 (4), 435 (1992).
Okubo, et al., *Colloid Polym. Sci.*, 274, 433 (1996).
Poulain, et al., *Polym. Sci.*, 34, 729 (1996).
Ringsdorf, et al., *Angew. Chem.*, 100, 117 (1988).
Schirmer, T. et al., *Science* 267, 512 (1995).
Schmidt, et al., *Polym. Prepr.*, 39, 725 (1998).
Wang, C, et al., *Nature* 397, 417 (1999).
Wang, Y.–F. et al., *J. Mol. Biol.* 272, 56 (1997).
Winterhalter, M., *Colloids and Surfaces A* 149, 547 (1999).
Won, Y.–Y. et al., *Science* 283, 960 (1999).
Yang, et al., *Colloid Polym. Sci.*, 270, 1080 (1992).
Yang, et al., *Macromolecules*, 25, 1786 (1992).
Yang, et al., *Macromolecules*, 25, 1791 (1992).
Zhang, et al., *Science*, 268, 1728 (1995).
Zhang et al., *Science* 272(5269), 1777–9 (1996).

* cited by examiner

AMPHIPHILIC POLYMERIC VESICLES

RELATED APPLICATION

This application claims priority to U.S. provisional application Ser. No. 60/163,678, filed on Nov. 5, 1999.

FIELD OF THE INVENTION

The present invention is generally in the field of vesicles. More specifically, the present invention is in the field of self-assembling polymeric vesicles with enhanced stability.

BACKGROUND OF THE INVENTION

Self-organizing, or self-assembling, structures are known. A common example is liposomes. Liposomes are made by emulsifying amphiphilic (and optionally hydrophobic or lipophilic) molecules in water, preferably in the presence of surfactant. Liposomes are either unilamellar or multilamellar spheres that are manufactured from a variety of lipids. Drugs, for example, can be encapsulated within liposomes or captured within the liposome membrane.

Self-assembled structures known in the prior art have often exhibited limited stability that induces, for example, a rapid clearance of drug-loaded vesicles from the blood after their intravascular administration. Various approaches to increasing stability have included cross-linked liposomes, which are more resistant to degradation. Liposomes having "pegylated" surfaces, i.e. surfaces having coated thereon or bonded thereto polyethylene glycol, have longer circulating times following administration to a patient. Other methods to prepare liposomes with enhanced stability include preparation techniques such as emulsion polymerization and interfacial polymerization. However, these techniques require rather aggressive reaction conditions, so sensitive substances cannot be used during these procedures. The stability of liposomes can be enhanced by surface grafting of hydrophilic polymers or by polymerization of reactive lipid molecules in the vesicular aggregates. Recently, a similar mechanical stabilization of vesicles was obtained by swelling the lipid bilayer of vesicles with hydrophobic monomers, which were subsequently polymerized.

Other approaches for the preparation of nanometer to micrometer-sized spherical polymer shells involve the layer-by-layer deposition of polyelectrolytes on the surface of a charged nanoparticle followed by the dissolution of the templating particle or the shelf-assembly of amphiphilic diblock copolymers into micelles, selective cross-linking of their hydrophilic shell, and subsequent degradation of the hydrophobic core. Although it has been known for several years that under suitable conditions amphiphilic block copolymers can aggregate spontaneously into vesicular structures, this direct formation of aggregates with a hollow sphere morphology has only been used in one case to prepare polymer nanocapsules. This approach used, however, a rather complex process. The formation of vesicles from a poly(isoprene)-block-poly(2-cinnamoylethyl methacrylate) (PI-PCEMA) diblock copolymer in hexane was followed by the photo-crosslinking of the PCEMA blocks and w subsequent selective hydroxylation of the PI blocks to make the hollow nanospheres soluble in water.

It is therefore an object of the present invention to provide new types of mechanically and chemically stable vesicles and nanocapsules, using the concept of self-organization of amphiphilic molecules.

It is a further object of the present invention to provide amphiphilic copolymers, in one example cross-linkable triblock copolymers, for use in the manufacture of these structures.

It is a further object to provide methods of making vesicles and nanocapsules from amphiphilic copolymers.

It is a further object to provide vesicles and nanocapsules made from amphiphilic copolymers having molecules inserted in the membrane wall, and methods of making such.

SUMMARY OF THE INVENTION

Vesicles are made from segmented amphiphilic A+B copolymers, where A is hydrophilic and B is hydrophobic, which self-assemble when dispersed in oil or water. In one embodiment, the vesicles are made from an ABA triblock copolymer, and where the inner core is hydrophilic, the middle layer is hydrophobic, and the outer shell is hydrophilic. In another embodiment, the vesicles are made from a BAB triblock copolymer. In another embodiment, the vesicles are made from an AB diblock copolymer. The copolymers are formed into vesicles and then polymerized or crosslinked for stability to form nanocapsules.

The vesicles may be stabilized by end group polymerization and/or by crosslinking of internal groups. The polymerization and crosslinking can be achieved via ionic bonds, covalent bonds, and/or through other types of bonds. In one embodiment, end groups of the copolymers are polymerized. The polymerization can be achieved by a number of means, such as photopolymerization, typically in the presence of a photoinitiator, or redox polymerization. In one embodiment, the vesicles are crosslinked to form nanocapsules, after encapsulation of an agent to be delivered.

The vesicles or crosslinked nanocapsules can be used for a number of purposes. In one embodiment, the nanocapsules are used to deliver a therapeutic, prophylactic, or diagnostic agent to a patient in need thereof. For example, if an ABA copolymer is used, a hydrophilic drug can be encapsulated inside the vesicles or a hydrophobic drug can be encapsulated in the middle layer of the vesicles.

In another embodiment, a molecule, such as a lipid membrane protein, is inserted into the vesicle membrane. Subsequent polymerization/crosslinking of the membrane does not render the molecule inactive.

In another aspect, methods for making vesicles and nanocapsules from amphiphilic copolymers are disclosed.

DETAILED DESCRIPTION OF THE PREFERRED EMBODIMENTS

Definitions

The term vesicles as used herein refers to spontaneously forming aggregates having a generally spherical shape and an interior void.

The terms nanospheres and nanocapsules are used synonymously herein and refer to vesicles that are stabilized through crosslinking. While the nanocapsules are generally in the nanometer size range, they can be as large as about 20 microns. Thus, the term is not limited to capsules in the nanometer size range. The capsules can be spherical in shape or can have any other shape.

The term polymerization as used herein refers to end to end attachment of the amphiphilic copolymers.

The term crosslinking as used herein refers to interpolymer linking of all types, including end to end attachment as well as covalent or ionic bonding of any portion of a copolymer to another copolymer. Crosslinking can be through end groups or internal groups and can be via covalent, ionic, or other types of bonds.

Segmented copolymers, containing at least one hydrophilic A segment and at least one hydrophobic B segment, that self-assemble to form vesicles, and methods for making such vesicles, are disclosed. The copolymers are primarily described herein as block copolymers. It should be understood that this term refers to linear block copolymers as well as various other structures, such as graft and comb structures, containing both A and B segments.

Various types of amphiphilic copolymers can be used. In one embodiment, the copolymer is an ABA copolymer, where A is hydrophilic and B is hydrophobic. A vesicle having hydrophilic inner and outer layers and a middle hydrophobic layer will be formed. In another embodiment, a BAB copolymer is used and a "reverse vesicle" will be formed, having hydrophobic inner and outer layers and a hydrophilic inner layer. In another embodiment, using an ABA copolymer where A is hydrophilic, in an aqueous/oil mixture, vesicles with U-shaped molecules can be formed, where each hydrophilic end of a copolymer is on the external surface of the vesicle and the hydrophobic middle segment of the copolymer is toward the interior void of the vesicle. The interior of the vesicle is oil filled. AB segmented copolymers can also be used, where the outside or inside of the vesicle is hydrophilic and the other side is hydrophobic, depending upon the liquid phase that is used.

The formation of vesicles from the copolymers is a result of the amphiphilic nature of the segmented copolymers. The aggregation occurs via non-covalent interactions and therefore is reversible. The vesicles can be crosslinked to provide additional stability. It should be understood that the copolymers can be polymerized via end groups, crosslinked via internal crosslinkable groups, or a combination of end group and internal group polymerization/crosslinking can be used. If the vesicles are crosslinked, the resulting nanocapsules are more stable, shape-persistent, and may preserve their hollow morphology even after they are removed from an aqueous solution.

The stability of a particular vesicle depends in a large part on the strength of the hydrophobic and hydrophilic interactions between the copolymers. The strength also depends upon the stability of the junction between the hydrophilic and hydrophobic segments, and the juncture between the hydrophilic or hydrophobic segment and the polymerizing unit, if one is used. The stability further depends upon the strength of the polymerization or crosslinking. The stability of the vesicle can be decreased by the introduction of weak links, such as biodegradable links or ionic crosslinks, between the hydrophilic and hydrophobic segments, within the hydrophilic or hydrophobic segment, or between the hydrophilic or hydrophobic segment and the polymerizing unit.

Crosslinking can be achieved using many standard techniques, including photopolymerization, for example, of acrylate groups in the presence of a photoinitiator, or through the use of an alkylating agent. Crosslinking can also be achieved using side groups and end groups which can be polymerized by free radical polymerization, side groups which can be polymerized by cationic polymerization, and side groups which can be polymerized by ring-opening polymerization.

In addition to the hydrophilic and hydrophobic segments, the membranes may also include additional hydrophobic and/or hydrophilic components, as well as crosslinkers such as monomers or macromers with reactive groups, surfactants, and crosslinking initiators, especially photoinitiators. Targeting or biological signal molecules can be attached to the outside surface of the vesicles.

I. The Amphiphilic Copolymers

The vesicles are formed of amphiphilic segmented copolymers including hydrophilic and hydrophobic segments. In one embodiment, the copolymers are ABA copolymers, where A is the same or different hydrophilic segments and B is a hydrophobic B segment.

One class of suitable polymeric materials is described in U.S. Pat. No. 5,807,944 to Hirt, et al. Since the materials disclosed therein are primarily for use as a contact lens, it is highly desirable that the materials be oxygen and ion-permeable. That is not a requirement for other applications, such as drug delivery, and in fact may not be desirable in some applications. In one embodiment, the amphiphilic polymer is biocompatible. Many suitable amphiphilic copolymers and hydrophobic and hydrophilic copolymers are described in WO 97/49387.

A. Hydrophilic and Hydrophobic Segments

The amphiphilic segmented copolymer includes at least one segment B that includes a hydrophobic polymer. Any of a number of hydrophobic polymers can be used, such as, but not limited to, polysiloxane such as polydimethylsiloxane and polydiphenylsiloxane, perfluoropolyether, polystyrene, polyoxypropylene, polyvinylacetate, polyoxybutylene, polyisoprene, polybutadiene, polyvinylchloride, polyalkylacrylate (PAA), polyalkylmethacrylate, polyacrylonitrile, polypropylene, PTHF, polymethacrylates, polyacrylates, polysulfones, polyvinylethers, and poly(propylene oxide), and copolymers thereof.

The hydrophobic segment preferably contains a predominant amount of hydrophobic monomers. A hydrophobic monomer is a monomer that typically gives a homopolymer that is insoluble in water and can absorb less than 10% by weight of water.

Suitable hydrophobic monomers are C1–C18 alkyl and C3–C18 cycloalkyl acrylates and methacrylates, C3–C18 alkylacrylamides and -methacrylamides, acrylonitrile, methacrylonitrile, vinyl C1–C18 alkanoates, C2–C18 alkenes, C2–C18 haloalkenes, styrene, (lower alkyl)styrene, C4–C12 alkyl vinyl ethers, C2–C10 perfluoro-alkyl acrylates and methacrylates and correspondingly partially fluorinated acrylates and methacrylates, C3 through C12 perfluoroalkylethylthiocarbonylaminoethyl acrylates and methacrylates, acryloxy- and methacryloxyalkylsiloxanes, N-vinylcarbazole, C1 through C12 alkyl esters of maleic acid, fumaric acid, itaconic acid, mesaconic acid, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobornyl methacrylate, trifluoroethyl methacrylate, hexa-fluoroisopropyl methacrylate, hexafluorobutyl methacrylate, tristrimethylsilyloxysilylpropyl methacrylate (TRIS), and 3-methacryloxypropylpentamethyldisiloxane.

In one embodiment, the hydrophobic polymer is one which displays a relatively high oxygen diffusion rate there through, such as, but not limited to, polysiloxanes, perfluoroalkyl ethers, specific unsaturated polymers, and polysulfones. In one embodiment, the hydrophobic polymer is a polysiloxane block having terminal alkylene groups.

In another embodiment, the hydrophobic polymer includes a perfluoroalkyl-polyether block. In another embodiment, the hydrophobic polymer includes an unsaturated polymer, such as a polymer of a conjugated aliphatic or alicyclic diene, which may be substituted by halogen or lower alkyl, a polymer of an alkyne or dialkyne, which may be substituted by lower alkyl or trimethylsilyl, a copolymer of a conjugated diene and a hydrophilic or hydrophobic vinylic monomer, and also partially hydrated derivatives of these compounds.

Specific examples of preferred polymers of conjugated dienes are cis-, trans-, iso- or syndiotactic poly-1,2-butadiene, poly-1,4-butadiene or polyisoprene, polypentenamer, polychloroprene and polypiperylen. Preferred examples of copolymers are butadiene- or isoprene-copolymers with hydrophilic or hydrophobic vinylic monomers, such as acrylonitrile, styrene, acrylic acid or hydroxyethylmethacrylate. An example of a polyalkyne is poly-1-trimethylsilyl-propyne. Especially preferred unsaturated polymers are syndiotactic poly-1,2-butadiene, poly-1,4-butadiene and polyisoprene. An especially preferred unsaturated polymer is poly-1-trimethylsilyl-propyne. Another especially preferred unsaturated polymer is poly-1,4-butadiene.

The hydrophobic polymer may include a single type of polymer or more than one type of polymer, such as two or more of those discussed above. The mean molecular weight of one segment B is in the range from about 500 to about 50,000, preferably in the range from about 800 to about 15,000, more preferably in the range of about 1,000 to 12,000, particularly preferably in the range from about 5,000 to about 12,000.

In addition to the hydrophobic segment B, the amphiphilic segmented copolymer includes at least one segment A which includes at least one hydrophilic polymer, such as, but not limited to, polyoxazoline, polyethylene glycol, polyethylene oxide, polyvinyl alcohol, polyvinylpyrrolidone, polyacrylamide, poly(meth)acrylic acid, polyethylene oxide-co-polypropyleneoxide block copolymers, poly(vinylether), poly(N,N-dimethylacrylamide), polyacrylic acid, polyacyl alkylene imine, polyhydroxyalkylacrylates such as hydroxyethyl methacrylate (HEMA), hydroxyethyl acrylate, and hydroxypropyl acrylate, polyols, and copolymeric mixtures of two or more of the above mentioned polymers, natural polymers such as polysaccharides and polypeptides, and copolymers thereof, and polyionic molecules such as polyallylammonium, polyethyleneimine, polyvinylbenzyltrimethylammonium, polyaniline, sulfonated polyaniline, polypyrrole, and polypyridinium, polythiophene-acetic acids, polystyrenesulfonic acids, zwitterionic molecules, and salts and copolymers thereof.

The hydrophilic segment preferably contains a predominant amount of hydrophilic monomers. A hydrophilic comonomer is a monomer that typically gives a homopolymer that is soluble in water or can absorb at least 10% by weight of water.

Suitable hydrophilic monomers are hydroxyl-substituted lower alkyl acrylates and methacrylates, acrylamide, methacrylamide, (lower alkyl) acrylamides and methacrylamides, N,N-dialkyl-acrylamides, ethoxylated acrylates and methacrylates, polyethyleneglycol-mono methacrylates and polyethyleneglycolmonomethylether methacrylates, hydroxyl-substituted (lower alkyl) acrylamides and methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino(lower alkyl)- (where the term amino also includes quaternary ammonium), mono(lower alkylamino)(lower alkyl) and di(lower alkylamino)(lower alkyl) acrylates and methacrylates, allyl alcohol, 3-trimethylammonium 2-hydroxypropylmethacrylate chloride (Blemer,QA, for example from Nippon Oil), dimethylaminoethyl methacrylate (DMAEMA), dimethylaminoethylmethacrylamide, glycerol methacrylate, and N-(1,1-dimethyl-3-oxobutyl) acrylamide.

In one embodiment, the segment A includes a polymer displaying a relatively high water or ion diffusion rate there through. Specific examples of hydrophilic monomers from which such polymers can be made are cyclic imino ethers, vinyl ethers, cyclic ethers including epoxides, cyclic unsaturated ethers, N-substituted aziridines, β-lactones and β-lactames. Further suitable monomers include ketene acetals, vinyl acetals and phosphoranes. Suitable cyclic imino ethers include 2-oxazoline. If a 2-oxazoline having an alkenyl group in 2 position is used as hydrophilic monomer, a polymerizable unsaturated group is provided within segment A (in a side chain) of the amphiphilic segmented copolymer to serve as the polymerizable unsaturated group necessary for the final polymerization to obtain a polymeric product or as an additional polymerizable unsaturated group which offers the possibility of direct crosslinking in the preparation of the polymer. The most preferred cyclic imino ether is 2-methyloxazoline. The most preferred vinyl ethers are methyl vinyl ether, ethyl vinyl ether and methoxy ethyl vinyl ether.

The mean molecular weight of one segment A is in the range from about 500 to about 50,000, preferably in the range from about 800 to about 15,000, more preferably in the range of about 1,000 to 12,000, particularly preferably in the range from about 5,000 to about 12,000.

B. Preparation of the Amphiphilic Copolymer

The segments A and B are linked together through a bond that may be hydrolyzable or non-hydrolyzable. A non-hydrolyzable bond is a covalent bond that is not cleaved by an ordinary aqueous or solvent hydrolysis reaction, e.g. under acidic or basic conditions. Specific bonds that are hydrolyzable are well known to those skilled in the art.

A non-hydrolyzable bond between segments A and B in the amphiphilic segmented copolymer can be formed by polymerizing a suitable hydrophilic monomer (from segment A) in the presence of a suitably functionalized hydrophobic monomer (from segment B) such that a block of units of the hydrophilic monomer grows from the site of functionalization of the hydrophilic monomer or, alternatively by polymerizing a suitable hydrophobic monomer in the presence of a suitably functionalized hydrophilic monomer such that a block of units of the hydrophobic monomer grows from the site of functionalization of the hydrophilic monomer.

The functionalized segment is also called a macroinitiator. Suitable macroinitiators include a thermally or photochemically activatable cationic or anionic groups, or a thermally or photochemically activatable radical initiator group. Anionic polymerization, polycondensation, and polyaddition can also be used. Specific examples of preferred photochemically activatable cationic initiator groups are triflate (—O—SO$_2$—CF$_3$), —I (iodide), —O-mesyl, —O-tosyl, and —Cl+ AgSbF$_6$. The most preferred initiator group is the triflate group. The initiator group is linked to the starting segment in a way that provides a covalent non-hydrolyzable bond between the terminal group of the starting segment and the first monomer forming the growing segment that is attached to the starting segment during the graft copolymerization for preparing the amphiphilic segmented copolymer. Grafting means that polymer chains are grown from a monomer either in terminal or in pendant position onto another preformed polymer.

The initiator group may be introduced into a preformed polymer in a suitable way, for example through linkage of cationic or thermal initiator groups to functional groups present on the starting monomer. Only the latter method is suitable for providing pendent initiator groups. Preferred triflate groups can be introduced by reaction of terminal or pendent functional hydroxyl groups with activated triflic acid derivatives such as (CF$_3$SO)$_2$O.

A degradable bond between the A segment and the B segment can be used so that the vesicle or nanocapsule can be degraded. Degradable bonds within the A or B segment can also be used. Biodegradable regions can be constructed from polymers or monomers using linkages susceptible to biodegradation. Degradability can be imparted by inclusion of a single degradable linkage or a degradable region made of more than one degradable linkage. The terms degradable linkage and degradable region are used interchangeably hereinafter.

The degradable region is preferably degradable under in vivo conditions. For example, a degradable region may be a hydrolyzable region, such as made from a polymer or oligomer of glycolide, lactide, ϵ-caprolactone, other hydroxy acids, or other biologically degradable polymer that yields materials that are non-toxic or present as normal metabolites in the body. Regions that are biodegradable by enzymatic degradation can also be used. Preferred poly(α-hydroxy acids) are poly(glycolic acid), poly(DL-lactic acid), and poly(L-lactic acid). Other useful materials include poly (amino acids), poly(anhydrides), poly(orthoesters), poly (phosphazines) and poly(phosphoesters). Polylactones such as poly(ϵ-caprolactone), poly(δ-valerolactone), and poly(γ-butyrolactone), for example, are also useful. The biodegradable region may have a degree of polymerization ranging from one up to values that would yield a product that is not substantially water soluble. Thus, monomeric, dimeric, trimeric, oligomeric, and polymeric regions may be used.

Accordingly, the amphiphilic segmented copolymers may consist in one embodiment of one segment A and one segment B (A-B-type, diblock), or of one segment A and two segments B attached to its termini (B-A-B-type, triblock), or may have a comb-type structure wherein several segments B are pendent from one segment A, which may further carry one or two terminal segments B). In another embodiment, the amphiphilic segmented copolymers may consist of one segment B and two segments A attached to its termini (A-B-A-type, triblock). In another embodiment, the amphiphilic segmented copolymers may have a comb-type structure wherein several segments A are pendent from one segment B, which may further carry one or two terminal segments A. Preferably, the copolymer is an ABA triblock copolymer.

It is also possible to change the monomer during graft copolymerization such that, for example, first hydrophilic segments A are grown on a preformed hydrophobic segment B and then hydrophobic segments B' are attached to the termini of the earlier prepared segments A. Also a different hydrophilic monomer may be used to produce a different hydrophilic segment A' at the termini of the hydrophilic segments A. Again, other embodiments of the amphiphilic segmented copolymers may be produced starting from a functionalized hydrophilic segment A.

The polymer that makes up the starting segment (A or B) usually has a number average molecular weight Mn in the range from about 500 to about 50,000, preferably in the range from about 800 to about 15,000, more preferably in the range of about 1,000 to 12,000, particularly preferably in the range from about 5,000 to about 12,000. The length of the one or more segments A, B, A', or B' which are to be graft copolymerized on the starting segment can be easily controlled by controlling the amount of monomer (hydrophilic or hydrophobic) which is added for the graft copolymerization. In this way the size of the segments and their ratio can easily be controlled.

The amphiphilic segmented copolymers can be prepared in the presence or absence of a solvent. It is advantageous to use a substantially inert solvent, i.e. one that does not participate in the reaction. Suitable examples are halogenated hydrocarbons, such as chloroform or methylene chloride, bipolar aprotic solvents, such as acetonitrile, acetone, dimethylformamide (DMF) or dimethyl sulfoxide (DMSO), hydrocarbons, such as toluene or xylene, and pyridine or N-methylmorpholine, and mixtures thereof.

In the preparation of the amphiphilic segmented copolymers of the invention, the reaction temperature can be, for example, from −60° C. to 150° C., preferably from 0° C. to 80° C. The reaction times are in the range from about 15 minutes to 7 days, preferably in the region of about 2 to 48 hours. If necessary, the reaction is carried out under argon or nitrogen as protective gas. A suitable catalyst, for example dibutyltin dilaurate (DBTDL), is added in the urethane-forming terminal functionalizing reaction.

C. Polymerization Groups

The segmented copolymers may already contain polymerizable groups in the hydrophobic and/or hydrophilic segments, e.g. if a hydrophobic segment B comprises a dienepolymer like polybutadiene or polyisoprene, or if the monomer used for making a hydrophilic segment comprises an unsaturated side chain, for example 2-allyl-oxazoline. Whether or not present, it is possible to introduce polymerizable groups by suitable reactions, e.g. at the end of or pendent from the growing segments. For this purpose, the graft polymerization of the growing segment may be terminated after a suitable chain length is reached and the initiator group present at the chain end capped, for example, either by using specific reagents such as hydroxy styrene, allyl alcohol, HEMA, propargyl alcohol, allyl amines and propargyl amine, or by using KOH/EtOH or primary amines leaving —OH or —NH— groups or unsaturated groups at the end of the growing segment. Hydroxyl groups may also be introduced into the copolymers by employing suitable comonomers in the graft copolymerization, e.g. 2-hydroxy-alkyloxazolines. The hydroxyl or —NH— groups may then be reacted, e.g. with an isocyanate carrying a polymerizable unsaturated group. Preferred examples of such bifunctional compounds are 2-isocyanatoethyl methacrylate (IEM), which is especially preferred, and vinyl isocyanate, allyl isocyanate, acryloyl isocyanate, styrene isocyanate, vinyl benzyl isocyanate, propargyl isocyanate, and (meth)acrylic anhydride. Other polymerizable groups can be introduced by methods known to those skilled in the art.

Any type of polymerization/crosslinking can be used. Examples include photopolymerization, redox polymerization, anionic polymerization, condensation reactions, addition reactions, and chain polymerization reactions.

D. Additional Monomers

In the preferred polymeric product, the proportion by weight of the amphiphilic segmented copolymer is in the range from 100 to 50%, in particular in the range from 100 to 80%, preferably in the range from 100 to 90%, based on the total polymeric product. The polymeric product may be obtained by direct thermal or photochemical polymerization or crosslinking reaction of the amphiphilic segmented copolymer without the addition of comonomers in the presence of a suitable initiator. However, in some cases, it may be preferable to include a comonomer. Types of comonomers that may be desired include hydrophobic or hydrophilic comonomers, or cationic or anionic comonomers. It may also be desirable to include a comonomer that contains a specific functional group, such as a crosslinkable group, or a group that has a particular affinity for a molecule to be incorporated into or onto the membrane, as discussed below. Suitable hydrophobic and hydrophilic comonomers include those discussed above.

The comonomers can be included within the amphiphilic polymer network, or crosslinked as an interpenetrating or semi-interpenetrating network with the amphiphilic polymer. Crosslinking may be achieved with the addition of a comonomer and/or a crosslinking agent, for example, a polyunsaturated comonomer.

E. Crosslinking Agents

A polymer network can, if desired, be reinforced by addition of a crosslinking agent, for example, a polyunsaturated comonomer. A crosslinked polymeric product including the product of the polymerization and crosslinking reaction of an amphiphilic segmented copolymer, can also be formed, if desired, with at least one vinylic comonomer and with at least one crosslinking agent. Crosslinking can be achieved by a number of different means, such as but not limited to, free radical crosslinking, redox crosslinking, and salt crosslinking.

Examples of suitable crosslinking agents include allyl methacrylate, lower alkylene glycol dimethacrylate, poly (lower alkylene) glycol dimethacrylate, lower alkylene dimethacrylate, divinyl ether, divinyl sulfone, di- and trivinylbenzene, trimethylolpropane trimethacrylate, pentaerythritol tetramethacrylate, bisphenol A dimethacrylate, methylenebis(meth)acrylamide, triallyl phthalate and diallylphthalate, α-ω-bis(methacryloxyalkyl)-oligosiloxanes such as bis(methacryloxypropyl) tetramethyldisiloxane, and perfluoroalkyl- or perfluoroalkylether-bismethacrylates.

The amount of crosslinking agent used is expressed in a proportion by weight based on the total polymer and is in the range from 20 to 0.05%, in particular in the range from 10 to 0.1%, preferably in the range from 5 to 0.1%.

F. Crosslinking Initiators

The polymeric products are crosslinked in a manner known in the art from the corresponding monomers (the term monomer here also including an amphiphilic segmented copolymer) by a polymerization reaction customary to the person skilled in the art.

In the case of monomers that can be crosslinked with free radical crosslinking, a mixture of monomers is typically warmed with addition of a free-radical former. Examples of such free-radical formers are azoisobutyronitrile (AIBN), potassium peroxodisulfate, dibenzoyl peroxide, hydrogen peroxide, and sodium percarbonate. If, for example, the compounds are warmed, free radicals form with homolysis, and can then initiate polymerization.

A polymerization reaction may be carried out using a photoinitiator that can initiate free-radical polymerization and/or crosslinking. Examples of suitable photoinitiators include benzoin methyl ether, 1-hydroxycyclohexylphenyl ketone, and Darocure and Irgacure products, preferably Darocure 1173® and Irgacure 2959®. Also suitable are reactive photoinitiators, which can be incorporated, for example, into a macromer, or can be used as a specific comonomer. Examples are described in European Patent No. EP 0 632 329. The photopolymerization can then be initiated by actinic radiation, for example light, in particular UV light having a suitable wavelength. The spectral requirements can, if necessary, be controlled appropriately by addition of suitable photosensitizers.

The polymerizable regions may be polymerizable by photoinitiation by free radical generation, most preferably in the visible or long wavelength ultraviolet radiation. Polymerizable regions are acrylates, diacrylates, oligoacrylates, dimethacrylates, oligomethoacrylates, or other biologically acceptable photopolymerizable groups. A preferred tertiary amine is triethanol amine.

Useful photoinitiators are those that can be used to initiate by free radical generation polymerization of the macromers without cytotoxicity and within a short time frame, minutes at most and most preferably seconds. Preferred dyes as initiators of choice for LWUV initiation are ethyl eosin, 2,2-dimethoxy-2-phenyl acetophenone, other acetophenone derivatives, and camphorquinone. In all cases, crosslinking and polymerization are initiated among copolymers by a light-activated free-radical polymerization initiator such as 2,2-dimethoxy-2-phenylacetophenone or a combination of ethyl eosin ($10^{-4}$–$10^{-2}$ milliM) and triethanol amine (0.001 to 0.1 M), for example.

The choice of the photoinitiator is largely dependent on the photopolymerizable regions. For example, when the macromer includes at least one carbon-carbon double bond, light absorption by the dye causes the dye to assume a triplet state, the triplet state subsequently reacting with the amine to form a free radical that initiates polymerization. Preferred dyes for use with these materials include eosin dye and initiators such as 2,2-dimethyl-2-phenylacetophenone, 2-methoxy-2-phenylacetophenone, and camphorquinone. Using such initiators, copolymers may be polymerized in situ by long wavelength ultraviolet light or by laser light of about 514 nm, for example. Lasers may be used to polymerize any nanospheres from a photopolymerizable solution, due to the precise control that can be achieved with the lasers. It is thus possible to make nanospheres as described herein without inclusion of the amphiphilic polymers.

Initiation of polymerization is accomplished by irradiation with light at a wavelength of between about 200–700 nm, most preferably in the long wavelength ultraviolet range or visible range, 320 nm or higher, most preferably about 514 nm or 365 nm. The light-sensitive free-radical polymerization initiator may be a single compound (e.g. 2,2-dimethoxy-2-phenyl acetophenone) or a combination of a dye and a cocatalyst (e.g., ethyl eosis and triethanol amine).

G. Solvents

Polymerization/crosslinking can be carried out in the presence or absence of a solvent. Suitable solvents are all solvents which dissolve the monomers used, for example, water, alcohols such as lower alkanols like ethanol or methanol, carboxamides such as dimethylformamide, dipolar aprotic solvents such as dimethyl sulfoxide or methyl ethyl ketone, ketones such as acetone or cyclohexanone, hydrocarbons such as toluene, ethers such as THF, dimethoxyethane or dioxane, halogenated hydrocarbons such as trichloroethane, and mixtures of suitable solvents such as mixtures of water and an alcohol, for example, a water/ethanol or water/methanol mixture.

II. Vesicles Formed from the Amphiphilic Copolymers

In general, vesicles can be made by a number of means known to those skilled in the art. Self assembly techniques are preferred. In one embodiment, the amphiphilic copolymer is dissolved in a solvent such as ethanol at a concentration of from about 5% to 30%. The polymer solution is then added to an aqueous solution (for an ABA copolymer), with stirring. This procedure generally leads to a dispersion of triblock copolymer vesicles of a rather broad size distribution. The size distribution can be controlled by methods known to those skilled in the art of preparing vesicles. In addition, the size distribution can be selected by passing the polydisperse vesicles through one or more filters having a defined pore size. The resulting vesicle dimensions are directly determined by the pore diameter of the filter membrane.

Polymerization

The amphiphilic copolymers can have polymerizable groups at both chain ends and/or can have internal polymerizable groups. These polymerizable groups can be polymerized after the formation of the self-assembled vesicle. Further crosslinking of polymerized vesicles can be achieved by incorporating crosslinkable groups into the copolymers, such as crosslinkable groups in the hydrophobic segments.

The nanocapsules maintain their shape even when they are removed from the aqueous solvent. The shape persistence of these nanocapsules is, particularly in context with some applications, of great interest. This stability of shape allows, for example, loading the particles with hydrophobic drug in an organic solvent, isolation of the loaded polymer shells, and subsequent release of the encapsulated material in an aqueous medium. The polymerized vesicles could be isolated from the aqueous solution by lyophilization. In contrast to the non-polymerized system, where this results in the formation of a waxy solid, the polymerized vesicle dispersion yields a fine colorless powder which can easily be redispersed in organic solvents (like chloroform or ethanol), or water.

Size

The diameter of the vesicles ranges from about 50 nm up to about 20 $\mu$m. Preferred size range depends on the specific application. For example, dyes for lipsticks or cars may be encapsulated with particles in the micrometer region. In contrast, pharmaceutical substances are preferably encapsulated with submicrometer particles.

Clearance of Vesicles

The uncrosslinked vesicles will degrade by dissolution and clearance through the kidney. Degradation for the crosslinked particles occurs through hydrolysis of the crosslinking bonds. More degradable bonds, such as anhydrides, or the other linkages discussed above, can be included to increase the degradation rate.

The block copolymer vesicles have comparable in vivo half-lives to the Stealth® liposomes (see D D Lasic: *Liposomes: from physics to applications*, Elesevier Science Publishers B.V., 1993).

III. Incorporation of Molecules into the Vesicles

The vesicles, especially the crosslinked nanocapsules, are suitable for delivery of nearly every type of therapeutic, diagnostic, or prophylactic agent (collectively referred to as "therapeutic agent" or "drug"). In one embodiment, the therapeutic agent is delivered to the target site via diffusion through the vesicle, and not by degradation of the vesicle. The polymer shell should be permeable to the agent in order to properly deliver the encapsulated drug.

Both hydrophilic and hydrophobic drugs, and large and small molecular weight compounds, can be delivered. Drugs can be proteins or peptides, polysaccharides, lipids, nucleic acid molecules, or synthetic organic molecules. Examples of hydrophilic molecules include most proteins and polysaccharides. Examples of hydrophobic compounds include some chemotherapeutic agents such as cyclosporine and taxol. These can be hormones, chemotherapeutics, antibiotics, antivirals, antifungals, vasoactive compounds, immunomodulatory compounds, vaccines, local anesthetics, antiangiogenic agents, antibodies, neurotransmitters, psychoactive drugs, drugs affecting reproductive organs, and antisense oligonucleotides. Diagnostic agents include gas, radiolabels, magnetic particles, radioopaque compounds, and other materials known to those skilled in the art.

Although described here primarily with reference to drugs, it should be understood that the vesicles can be used for delivery of a wide variety of agents, not just therapeutic or diagnostic agents. Examples include fragrances, dyes, photoactive compounds, reagents for chemical reactions, and other materials requiring a controlled delivery system.

Large quantities of therapeutic substances can be incorporated into the central cavity of the vesicles. Since the volume of the polymeric shell is rather low, relatively smaller amounts of therapeutic substances can be incorporated in the outer shell.

The drugs may be encapsulated into the polymer by at least two different routes. In one method, the drug may be directly added to the copolymer during preparation of the copolymer. For example, the drug may be dissolved together with the polymer in ethanol.

In a second method, the drug is incorporated into the copolymer after covalent crosslinking. The crosslinked vesicles can be isolated from the aqueous solution and redissolved in a solvent such as ethanol. Ethanol is typically a good solvent for the hydrophilic and the hydrophobic parts of the polymer. Hence, the polymer shell of the vesicles swells in ethanol and becomes permeable. Transferring the particles back into water decreases the permeability of the shell.

The vesicles can be targeted to a particular site using targeting molecules bound to the surface, or extending from within to the surface, of the vesicles, where the molecules specifically or preferentially bind to a particular cell or tissue specific site. Examples of targeting molecules include carbohydrates, proteins, folic acid, peptides, peptoids, and antibodies. The list of useful ligands to facilitate binding to mucous type tissues include sialic acid, neuraminic acid, n-acetyl-neuraminic acid, n-glycolylneuraminic acid, 4-acetyl-n-acetylneuraminic acid, diacetyl-n-acetylneuraminic acid, glucuronic acid, iduronic acid, galactose, glucose, mannose, and fucose. Antibodies may be directed to specific cell surface molecules or to antigens expressed when a cell type becomes diseased, for example, a cancer marker.

In another embodiment, molecules are inserted into the vesicle membrane wall. Many different types of molecules can be inserted into the vesicle wall, including peptides and proteins, lipids, polysaccharides, inorganic molecules, organic molecules, and nucleic acids. Hydrophobic or amphiphilic molecules are more easily incorporated into the wall, if it is made of an ABA copolymer, where B is hydrophobic. The amount of the molecule that can be incorporated will depend on many factors, including its molecular weight, hydrophobicity, and charge, and can be readily determined by one of skill in the art. In one embodiment, the molecule is a biological molecule, such as a protein, and especially preferred are membrane proteins, or proteins that typically exist within a biological membrane.

The vesicles or nanocapsules having an incorporated molecule can thus function as nanoreactors, where the molecule serves a gating function or a more active function.

Examples of membrane proteins include general transport proteins such as the bacterial porin OmpF, specific transport proteins such as maltoporin and LamB, active transport proteins such as Na-K-pump, phosphotransferases, and bacteriorrhodopsin, and immunoglobulins, such as IgG, T-cell receptors, CD4, CD8, and N-CAM.

The molecule can be incorporated during formation of the vesicle, by including it in the polymer solution. The molecule can also or alternatively be incorporated into the vesicle wall after the vesicle has been formed. In one embodiment, a biological molecule is inserted into the vesicle wall after the vesicle has been formed by including the molecule in a solution on one side of the vesicle. Insertion of the molecule into the vesicle wall can often be accelerated by applying a potential across the membrane.

The molecule can be incorporated into the vesicle wall before or after the membrane is polymerized and/or crosslinked, although in some cases, a large molecule may be ejected from the vesicle during polymerization or crosslinking.

IV. Uses for the Vesicles and Nanocapsules

As described in more detail above, the vesicles and nanocapsules can be used for drug delivery. Other applications include removal of contaminants from aqueous or non-aqueous solutions, recording materials, hydraulic fluids, coatings, chromatography, catalysis, and as filler and reinforcement agents for plastics.

The present invention will be further understood by reference to the following non-limiting examples.

EXAMPLES

The synthesis of a poly(2-methyloxazoline)-block-poly (dimethylsiloxane)-block-poly(2-methyloxazoline) (PMOXA-PDMS-PMOXA) triblock copolymer carrying polymerizable groups at both chain ends is described in Example 1. The synthesis of this material is also described in Nardin, C., Hirt, T., Leukel, J., Meier, W., *Langmuir*, 2000, 16, 1035.

The formation of vesicles from this triblock copolymer is described in Example 2, as well as subsequent polymerization of the polymer.

The physical properties of the vesicles before and after polymerization are characterized in Example 3 and the results compared with conventional liposomes.

The incorporation of a protein into vesicles is described in Example 4.

Example 1

Synthesis of PMOXA-PDMS-PMOXA Diblock and Triblock Copolymers

Bifunctional poly(dimethylsiloxane)

In a 250 mL round bottom two-necked flask with a Soxhlet extractor (filled with molecular sieve (4 A)), a condenser and a septum on the second ground joint, 34.2 g (6.34 mmol) α-ω-bis(3-hydroxypropyl)-polydimethylsiloxane (I<15, Wacker Chemie, additionally purified over a thin-film evaporator; Mw=5400 g mol$^{-1}$) were dissolved in 90 mL hexane and distilled under reflux for 17 h in a nitrogen atmosphere. After this drying procedure, the solution still contained 21 ppm water. Subsequently, the solution was concentrated to 60 mL hexane, cooled to 0° C. and 3.6 g (45.5 mmol) of dry pyridine were added. Then, 12.4 g (43.9 mmol) trifluoromethane sulfonic acid anhydride were added over 15 minutes and the mixture was stirred for another 30 min at a temperature of 0° C. After the addition of 20 mL chloroform (water content <10 ppm), the resulting suspension was filtered under vacuum using a G4 glass filter funnel. The solvent was evaporated under high vacuum.

The yield was 21.5 g of oil of orange color. This oil was in turn dissolved in 40 mL of dry hexane, activated charcoal was added, and the mixture was then stirred for about 2 min and filtered again. After evaporation of the solvent, the yield was 19.0 g of clear colorless oil. $^1$H-NMR (CDCL$_3$, 250 MHz): 0 ppm (CH$_3$—Si), 0.5 ppm (—CH$_2$—CH$_2$—Si), 1.8 ppm (—CH$_2$CH$_2$—CH$_2$—), 4.4 ppm (CF$_3$SO$_3$CH$_2$—CH$_2$—). Functionality >95% based on the $^1$H-NMR data.

Poly (2-methyloxazoline)-block-poly(dimethylsiloxane)-block-poly(2-methyloxazoline) (PMOXA-PDMS-PMOXA) triblock copolymer with free hydroxy end groups.

5.04 g (59.2 mmol) freshly distilled 2 methyl-2-oxazoline and 8.05 g (1.4 mmol) of the bifunctional PDMS were added to 15 mL 1.2-dichloroethane (water content <5 ppm) at room temperature. The solution was then stirred for 1.5 h and subsequently heated to 40° C. After 48 hr, the solution was cooled again to room temperature and 5.5 mL of a 0.5 M KOH solution in ethanol were added. The resulting solution was stirred for one hour and subsequently the solvent was evaporated under high vacuum. The yield was 12.0 g of colorless solid polymer.

$^1$H-NMR (CDCL$_3$, 250 MHz): 0 ppm (CH$_3$—Si), 2.0–2.1 ppm (CH$_3$CON<), 3.3–3.5 ppm (>N—CH$_2$—CH$_2$—N<). Functionality >95% according to OH titration (>0.4 mEq g$^{-1}$). GPC in THF revealed a molecular weight of the triblock copolymer of M$_n$=9000 g mol$^{-1}$ and a polydispersity of M$_w$/M$_n$=1.7. Consequently, the molecular weight of the two poly-2-methyloxazoline blocks was M$_n$=1800 gmol$^{-1}$, respectively.

PMOXA-PDMS-PMOXA Triblock Copolymers with Polymerizable End Groups

In a round bottom flask, 7.68 g (1.32 mmol) of the hydroxy-functionalized PMOXA-PDMS-PMOXA triblock copolymer were dissolved at room temperature in 20 mL dry ethyl acetate (water content<10 ppm). To this solution were added 420 mg (2.7 mmol) of 2-isocyanato-ethylmethacrylate (IEM) and about 40 mg dibutyltin dilaureate. The solution was stirred for 48 h in the absence of light. Afterwards, the solvent was evaporated under high vacuum for 5 h at a temperature of 0° C. The raw product was purified using ultrafiltration in a water/ethanol mixture to remove low molecular weight impurities. 6.89 g of the colorless solid polymer were obtained.

$^1$H-NMR (CDCL$_3$, 250 MHz): 0 ppm (CH$_3$—Si), 2.0–2.2 ppm (CH$_3$—CO), 3.3–3.5 ppm (>N—CH$_2$—CH$_2$—N<, >N—CH$_2$—CH$_2$—O<), 5.5 ppm (CH$_2$=), 6.1 ppm (CH$_2$=).

Functionality >95% according to $^1$H-NMR.

The molecular weight (Mw) of the material was 9000 gmol$^{-1}$ and the molecule includes a flexible hydrophobic PDMS middle block of 5400 gmol$^{-1}$ and two hydrophilic PMOXA blocks each of 1800 gmol$^{-1}$. The polydispersity was determined to be M$_w$/M$_n$=1.7.

The linear PMOXA-PDMS-PMOXA triblock copolymers exhibit lyotropic liquid crystalline phases in concentrated aqueous solutions. At room temperature, the polymer showed a broad miscibility gap on the water-rich side of the phase diagram, which extended up to about 50 wt % polymer. Above this concentration, the polymer follows a lamellar liquid crystalline phase.

Example 2

Preparation of Vesicles from PMOXA-PDMS-PMOXA

The formation of small unilamellar vesicles from the triblock copolymer was achieved according to the following procedure.

The end-group functionalised PMOXA-PDMS-PMOXA triblock copolymer was dissolved in ethanol to yield a clear, homogeneous solution containing 17 wt % polymer. This solution was added dropwise under vigorous stirring to the respective volume of doubly distilled water. The procedure led to a dispersion of triblock copolymer vesicles of a broad size distribution.

The polydispersity was reduced by extrusion of the vesicular dispersion through a Nucleopore filters (Millipore) having a pore size of 200 nm.

Polymerization of the vesicles was achieved by irradiating the dispersion for 15 min with an UV lamp (Ultratech 400 W, wavelength=254 nm, Osram AG). If stored in the dark to prevent their polymerization, the PMOXA-PDMS-PMOXA triblock copolymer vesicles were stable over several weeks and displayed no changes in size or size distribution within experimental accuracy after this period.

Example 3

Characterization of Vesicles from PMOXA-PDMS-PMOXA

Freeze-fracture Replication Transmission Electron Microscopy

A sample of approximately 10 microliters of the vesicle dispersion was brought onto a gold platelet at room temperature and was quenched by hand plunging into a mixture of 15% 2-methyl butane and 85% propane at 83 K. After quenching, the sample was transferred into liquid nitrogen and clamped on a brass block (Balzer). It was mounted on a Balzer freeze etch device (BAF 300), and subsequently the pressure was reduced to $5 \cdot 10^{-9}$ mbar. After evacuation, the sample was fractured with a liquid nitrogen cooled microtome. To enhance the contrast of the surface structure, the sample was warmed to 153 K and etched for 10 min. Thereafter, the sample was cooled again with liquid nitrogen and shadowed with W/Ta under an angle of 30°. After the samples were warmed up to room temperature and brought to atmospheric pressure, the replica was washed with chloroform, put on a 400 mesh copper TEM grid, and examined with an Hitachi H-8000 electron microscope operating at 100 keV.

The micrograph clearly showed that the preparation procedure yields spherical vesicles. The diameters of the displayed particles ranged from about 50 nm up to about 250 nm.

Static and Dynamic Light Scattering (SLS and DLS, Respectively).

The static and dynamic light scattering experiments were performed using a commercial goniometer (ALV-Langen) equipped with a frequency-doubled NdYAg laser (ADLAS, wavelength=532 nm) at scattering angles between 30° and 150°. An ALV-5000/E correlator calculates the photon intensity autocorrelation function $g^2$ (1). The samples were prepared by filtering the solutions through Millipore filters (HN 0.45 $\mu$m) into 10 mm quartz cells. These cells were mounted in a thermostated optical matching vat with a temperature accuracy of T=0.02 K. The experiments were performed at T=293 K.

The refractive index increment dn/dc was obtained at the corresponding temperature and wavelength of the light scattering experiments by using a commercial ALV-DR-1 differential refractometer. The data of DLS were analyzed using a Williams-Watts function [Williams, et al. *Trans. Faraday Soc.*, 1970, 66, 80; Williams, et al. *Trans. Faraday Soc.*, 1971, 67, 1323; Lindsey, et al. *J. Chem. Phys.*, 1980, 73, 3348]. The size polydispersity of the vesicles was determined according to reference [Van Zanten. *In Vesicles*; Rosoff, M.; Marcel Dekker, Inc.: New York, 1996; Vol. 62, p 240; Van Zanten, et al. *J. Colloid and Interface Science*, 1991, Vol. 146, 330; Ruf, et al. *Methods in Enzymology*, 1989, Vol. 172, 364].

The polydispersity of the resulting vesicles was determined to be about 20% from dynamic light scattering which is in good agreement with values reported for conventional extruded vesicles constituted from low molecular weight lipid molecules.

A typical Zimm diagram, with only the extrapolated values at zero scattering angle plotted, shows that the non-polymerized triblock copolymer vesicles at a minimum at about $1.7 \cdot 10^{-3}$ gmL$^{-1}$ is observed in the concentration dependence of static light scattering. Around this concentration, the radius of gyration $R_g$ exhibits a maximum. The mutual translational diffusion coefficient $D_m$, shows a break in the slope of the concentration profile. This behavior is typical of a closed association, like in micelle formation where monomers aggregate up to a certain concentration. In the present case, that means that there is a critical aggregation concentration (cac) below which the vesicular aggregates disintegrates into singly dissolved triblock copolymer molecules. Details about the aggregates, i.e. the triblock copolymer vesicles can be obtained by extrapolating the measurement at $c>2 \cdot 10^{-3}$ g mL$^{-1}$. Similarly, extrapolation of the data in the region below the cac should yield information about the single triblock copolymer molecules. Assuming that near the cac, individual triblock copolymer molecules and vesicles coexist, the intensity of the scattered light can be represented as the sum of the intensities due to the respective component. The critical aggregation concentration is calculated to be cac= $0.15 \cdot 10^{-3}$ g L$^{-1}$ (i.e. $1.6 \cdot 10^{-5}$ mol L$^{-1}$), which is comparable to that of typical low molecular weight lipids and depends significantly on the length of the individual hydrophilic and hydrophobic blocks of the triblock copolymer molecule. The occurrence of the cac at this concentration was also confirmed by surface tension measurements on the vesicle dispersions. This is due to the UV-induced crosslinking polymerization of the methacrylate end groups of the triblock copolymer molecules. The polymerization leads to a rather high conversion. Consequently, all the triblock copolymer molecules are covalently attached to the newly formed polymer network structure within the vesicles and, hence, they are no longer able to leave the aggregate upon dilution. The results of static and dynamic light scattering on both the polymerized and the non-polymerized vesicles are summarized in Table 1.

Table 1: Results from both dynamic and static light scattering experiments performed on vesicles and cross-linked nanospheres.

| Parameter | Vesicles in water | Crosslinked nanospheres in water |
|---|---|---|
| dn/dc (refractive index increment) (mL g$^{-1}$) | 0.188 | 0.187 |
| cac (critical aggregation concentration) (g ml$^{-1}$) | 0.15 × 10$^{-3}$ | Not measured |
| M (weight-average molecular weight) (10$^6$ g mol$^{-1}$) | 11 | 11 |
| A$_2$ (second virial coefficient) (mol ml g$^{-2}$) | 2 × 10$^{-6}$ | 2 × 10$^{-6}$ |
| R$_g$ (radius of gyration) (nm) | 127 | 124 |
| D$_0$ (diffusion coefficient) (10$^{-8}$ cm$^2$ s$^{-1}$) | 1.7 | 1.9 |
| R$_h$ (hydrodynamic radius) (nm) | 126 | 113 |
| k$_d$ (diffusion virial coefficient) (ml g$^{-1}$) | −18 | −24 |
| p (aggregation number with p = M$_v$/M$_p$) | 1220 | 1220 |
| ρ (p-parameter with p = R$_g$/R$_h$) | 1.008 | 1.097 |

No change in the average molecular weight, the dimensions, or the polydisperity of the aggregates was noted upon polymerization. This reflects that the free radical polymerization occurs only intravesicularly since intervesicular exchange of individual triblock copolymer molecules would result in an increase of their average aggregation number p (i.e. the molecular weight of the particles), particle dimensions and size polydispersity of the vesicles. Furthermore, the light scattering data also support the hollow sphere morphology of the particles. The radius of gyration R from static light scattering and the hydrodynamic radius R$_h$ from dynamic light scattering are found to be nearly identical for both the non-polymerized and the polymerized triblock copolymer vesicles, thus leading to a ratio p=R/R$_h$ of p=1.097, respectively. This so-called p-parameter is a structure sensitive property reflecting the radial density distribution of the scattering particle. A ratio of p=1 is characteristic for spherical shells.

Dynamic light scattering investigations on nanocapsules lyophilized and then redispersed in ethanol yield a hydrodynamic radius of R$_h$–90 nm. This is in reasonably good agreement with the value of the original polymerized particles in water which was determined to be Rh=113 nm.

Scanning Electron Microscopy (SEM)

A drop of the non-extruded crosslinked vesicle dispersion in water was put on a silicium wafer. After evaporation of the water the sample was examined with a Philips SL30 SEM. SEM micrographs of the vesicles formed by polymerization of a non-extruded-vesicle dispersion support the conclusion that the nanocapsules are shape persistent and preserve their hollow sphere morphology even after their isolation from the aqueous solution.

Transmission Electron Microscopy (TEM)

The samples were prepared by negative staining of the crosslinked vesicle dispersion with 2% uranyl acetate solution. They were deposited on a carbon-coated copper grid and examined with a Philips EM400. TEM micrographs of nanocapsules isolated from water by lyophilisation and redispersed in ethanol reflect a close packing of spherical nanocapsules. The diameters of the particles are in the range from about 50 nm to about 250 nm. The presence of a considerable amount of smaller particles and no larger ones supports the assumption of an ice crystal mediated disruption of the particles.

Surface Tension Measurements

The surface tension γ of the polymerized and the non-polymerized vesicle dispersions was determined with a Krüss K8 tension balance interfacial tensiometer thermostated at 25° C. using the Du-Noüy-ring method. The critical aggregation concentration (cac) of the triblock copolymer dispersions was deduced from the discontinuity in the γ (In c$_{polymer}$) curve and was found to be 0.15 10$^{-3}$ g mL$^{-1}$ (or 1.6 10$^{-5}$ mol L$^{-1}$) in agreement with the light scattering data. For the polymerized vesicles, no cac could be detected in the concentration regime investigated.

Example 4

Reconstitution of Channel Proteins in ABA Triblock Copolymer Vesicles

For the reconstitution experiments, the well-characterized bacterial porin OmpF was used as a model system [Nikaido, H., *Molecular Microbiology*, 1992, 6, 4, 435; Winterhalter, M., *Colloids and Surfaces A*, 1999, 149, 547; Schiermer, T., Keller, T. A., Wang, Y-F., Rosenbusch, J. P., *Science*, 1995, 267, 512; Eisenberg, B., *Acc. Chem. Res.*, 1998, 31, 117]. This porin is a transmembrane protein that forms trimeric channels in the outer membrane of Gram-negative bacteria. These water-filled channels allow passive diffusion of small solutes like ions, nutrients or antibiotics across the membrane. The incorporation of the porin into a vesicle can directly be monitored using the ability of β-lactamase to hydrolyze ampicillin to ampicillinoic acid. In contrast to ampicillin, the ampicillinoic acid can reduce iodine to iodide which can be measured by micro-iodometry, i.e. via the decolorization of the starch-iodine complex.

A porin stock solution (13.3 mg mL$^{-1}$ in 1 wt % octyl-polyoxyethylene, 100 mM NaCl, and 2.5 mM Hepes, pH 7.4) was mixed with a 17 wt % solution of the triblock copolymer in ethanol to a final molar ratio of 1:1000 (protein:polymer). For encapsulation of the enzyme β-lactamase in the interior of the vesicle, the solution was slowly added to an aqueous β-lactamase solution (0.024 mg/ml in 10 mM Hepes, 100 mM NaCl, pH 7.4) to a final copolymer concentration of 1 wt %. The resulting dispersion was extruded through Nucleopore filters, pore width 200 nm, resulting in a monodisperse collection of vesicles having an average diameter of 250 nm$^3$. Non-encapsulated protein was removed by chromatography over Sephadex G-200.

The vesicles were polymerized by irradiating the vesicle dispersion for 2 minutes with uv light.

Figure 1:
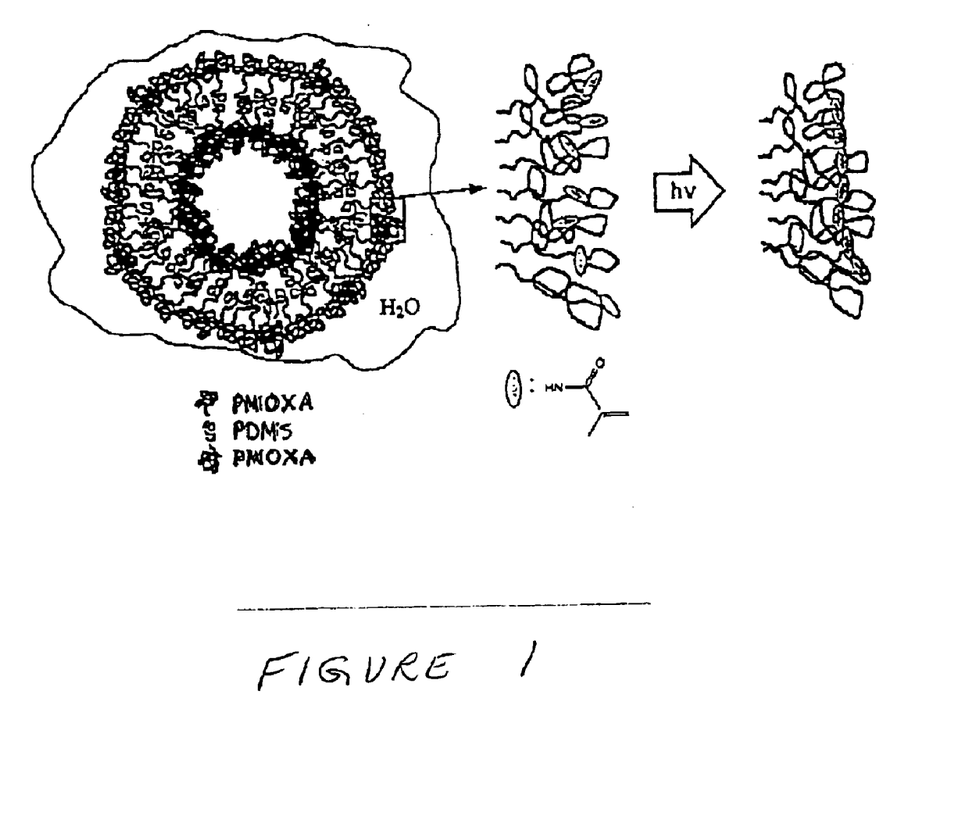
FIG. 1 is a schematic representation of a PMOXA-PDMS-PMOXA triblock copolymer vesicle in water and of the intravesicular crosslinking of the individual triblock copolymers through UV-irradiation of the polymerizable end-groups of the triblock copolymers to form a nanocapsule.
Figure 2:
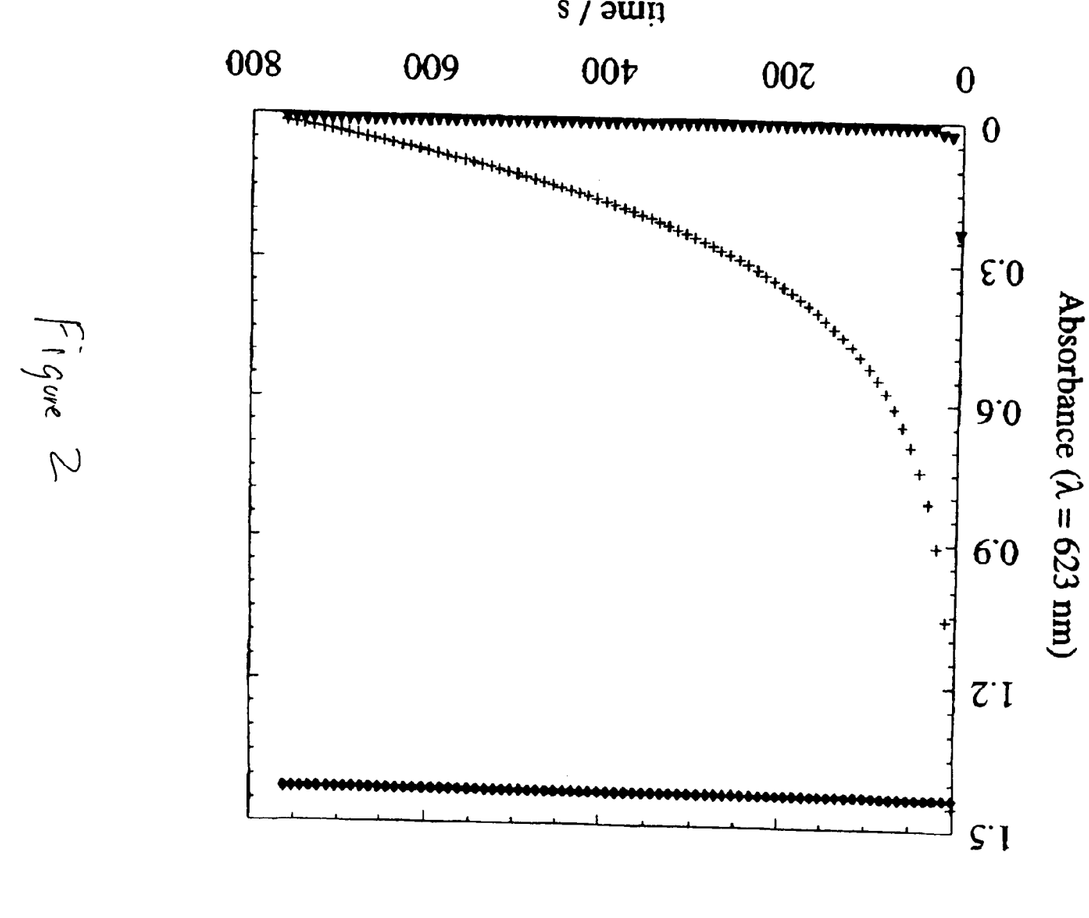
FIG. 2 is a time profile of the absorbance of starch-iodine complex at 623 nm after 30 minutes incubation in the presence of 10 $\mu$l of a 1 mM ampicillin solution. The plus signs represent the constructed nanoreactors, the filled triangles represent free, unincorporated enzyme, and the filled diamonds represent nanocapsules without incorporated enzyme or free enzyme.

10 μl of a 1 mM ampicillin solution (in 10 mM Hepes, 100 mM NaCl, pH 7.4) was added to the nanocapsule dispersion and the mixture incubated for 30 minutes. Starch iodine reagent was prepared by mixing 5 ml of a 8 mM iodine, 320 mM potassium iodide solution with 20 ml 1M sodium wolframate in 2 M acetic acid and then adding 5 ml of 2 wt % soluble starch which had been dissolved in 1 M acetic acid by boiling gently for 3 minutes. Subsequently, 0.5 ml of the starch-iodine reagent was added to the nanocapsule mixture and the absorbance of the starch-iodine complex was at 623 nm was measured as a function of time. The results are shown in FIG. 2, where the plus signs represent the constructed nanoreactors, the filled triangles represent free, unincorporated enzyme, and the filled diamonds represent nanocapsules without incorporated enzyme or free enzyme.

The absorbance remained constant for the nanocapsules without incorporated porin. In contrast, for the porin containing nanocapsules, the absorbance decreased slowly with time. The reaction rate of the vesicle-incorporated porins is, however, slower than that with free enzyme.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. Hollow vesicles comprising membranes formed from amphiphilic copolymers having hydrophobic and hydrophilic segments, wherein the copolymers are ABA copolymers, and wherein one of A and B is hydrophobic and the other is hydrophilic.

2. Hollow nanocapsules formed by stabilization of the vesicles of claim 1.

3. Hollow nanocapsules formed by stabilization of vesicles comprising membranes formed from amphiphilic copolymers having hydrophobic and hydrophilic segments, wherein the vesicles are stabilized by end group polymerization of the copolymers.

4. The nanocapsules of claim 2, wherein the vesicles are stabilized via crosslinking of the copolymers.

5. The nanocapsules of claim 3, wherein the copolymers are AB copolymers, wherein one of A and B is hydrophobic and the other is hydrophilic.

6. The nanocapsules of claim 3, wherein an active agent is encapsulated within the nanocapsule.

7. The vesicles of claim 1, wherein an active agent is encapsulated within the vesicle.

8. The nanocapsules of claim 2, wherein an active agent is encapsulated within the nanocapsule.

9. The vesicles of claim 1, wherein the vesicles comprise a hydrophilic inner layer, a hydrophobic middle layer and a hydrophilic outer layer.

10. The vesicles of claim 1, wherein the vesicles comprise a hydrophobic inner layer, a hydrophilic middle layer and a hydrophobic outer layer.

11. The vesicles of claim 1, wherein the copolymers are U-shaped and the vesicles have a hydrophobic inner layer and a hydrophilic outer layer, or a hydrophilic inner layer and a hydrophobic outer layer.

12. The nanocapsules of claim 3, wherein the polymerization is via photopolymerization.

13. The vesicles of claim 1, wherein one or more molecules are incorporated into the vesicle membrane.

14. The nanocapsules of claim 2, wherein the hollow morphology of the nanocapsules is preserved when the nanocapsules are dry.

15. The vesicles of claim 1, wherein the vesicles are biodegradable.

16. The nanocapsules of claim 2, wherein the nanocapsules are biodegradable.

17. The vesicles of claim 1 further comprising targeting molecules bound to the surface of the vesicles.

18. The vesicles of claim 17 wherein the targeting molecules are selected from the group consisting of carbohydrates, proteins, folic acid, peptides, peptoids, and antibodies.

19. The nanocapsules of claim 3, wherein the hollow morphology of the nanocapsules is preserved when the nanocapsules are dry.

20. The nanocapsules of claim 3, wherein the nanocapsules are biodegradable.

* * * * *